United States Patent [19]
Whitmore, III et al.

[11] Patent Number: 6,036,632
[45] Date of Patent: Mar. 14, 2000

[54] STERILE DISPOSABLE TEMPLATE GRID SYSTEM

[75] Inventors: Willet F. Whitmore, III; Winston E. Barzell; Roger F. Wilson, all of Sarasota, Fla.

[73] Assignee: Barzell-Whitmore Maroon Bells, Inc., Sarasota, Fla.

[21] Appl. No.: 09/085,011

[22] Filed: May 28, 1998

[51] Int. Cl.[7] ................................................. A61N 5/00
[52] U.S. Cl. ............................................. 600/7; 604/116
[58] Field of Search ........................... 600/1–8; 604/116; 606/71, 130

[56] References Cited

U.S. PATENT DOCUMENTS

| | | | |
|---|---|---|---|
| 3,508,552 | 4/1970 | Hainault | 128/303 |
| 3,817,249 | 6/1974 | Nicholson | 128/303 B |
| 4,167,179 | 9/1979 | Kirsch | 128/1.2 |
| 4,402,308 | 9/1983 | Scott | 128/1.2 |
| 4,427,005 | 1/1984 | Tener | 128/303 R |
| 4,580,561 | 4/1986 | Williamson | 128/303 B |
| 4,586,490 | 5/1986 | Katz | 128/1.1 |
| 4,642,096 | 2/1987 | Katz | 604/116 |
| 4,798,212 | 1/1989 | Arana | 128/749 |
| 4,998,912 | 3/1991 | Scarbrough et al. | 600/6 |
| 5,098,383 | 3/1992 | Hemmy et al. | 604/116 |
| 5,242,373 | 9/1993 | Scott et al. | 600/7 |
| 5,678,549 | 10/1997 | Heywang-Koebrunner et al. | 606/130 |
| 5,681,327 | 10/1997 | Heywang-Koebrunner | 606/130 |
| 5,702,405 | 12/1997 | Heywang-Koebrunner | 606/130 |
| 5,769,779 | 6/1998 | Alderson | 600/1 |

OTHER PUBLICATIONS

Martinez, A., M.D. et al., "A Multiple–Site Perineal Applicator (MUPIT) For Treatment of Prostatic, Anorectal, and Gynecologic Malignancies," *International Journal of Radiation, Oncology, Biology and Physiology Technical Innovations and Notes*, 10(2):1–9, Feb. 1984.

*Primary Examiner*—John P. Lacyk
*Attorney, Agent, or Firm*—Pennie & Edmonds LLP

[57] ABSTRACT

A sterile disposable template grid system for positioning and implanting medical implants is disclosed. In one embodiment, the disposable template grid includes an attachment element that joins a front portion having front channels and a rear portion having rear channels so that the front channels align with the rear channels to form passages which allow medical implants to pass from the front portion through the rear portion. In another embodiment, the disposable template grid includes an insert having channels; a bracket sized to removably receive and support the insert and having apertures; and an alignment element for aligning the apertures with the channels to allow medical implants to pass from the apertures through the channels. Although the disposable template grid can be used with a wide variety of implants, it is particularly well suited for the radioactive seed containing needles used in brachytherapy.

21 Claims, 6 Drawing Sheets

STERILE DISPOSABLE TEMPLATE GRID SYSTEM

FIELD OF THE INVENTION

This invention relates generally to a template grid system for positioning medical implants, and more particularly to a sterile disposable template grid system for use with transrectal ultrasound imaging probes in brachytherapy for cancerous prostate and related surgeries.

BACKGROUND

In 1997, the American Cancer Society estimated that 317,000 American men were diagnosed with prostate cancer. Traditional treatment with radiation and surgery are associated with significant side effects and one currently widely applied and popular method for the treatment of prostate cancer is the percutaneous transperineal implantation of radioactive seeds of either Iodine-125 or Palladium-103 called brachytherapy. This form of treatment for prostate cancer has been increasing in popularity because of minimal patient morbidity compared to other available treatments and the potential for improved efficacy due to increasingly accurate methods of seed placement.

Brachytherapy is performed with the patient in the lithotomy position, using an ultrasound imaging probe placed in the rectum to monitor seed placement. A template grid arrangement, which is kept in precise linear orientation with the ultrasound probe, must be accurately oriented adjacent the perineum in relation to the prostate, and locked in position throughout the procedure to achieve optimum seed placement. Precise and reproducible orientation and positioning of the ultrasound imaging probe in the rectum is a key element in both the calculations required for determining the number and distribution of radioactive seeds required for treatment and their subsequent placement using pre-loaded needles guided by the perineal template and real time ultrasound imaging. Even with proper probe positioning, placement of the seed-delivering needles using the template grid needs to be accurate and precisely coordinated with the images from the probe and the patient's anatomy to have effective therapy.

One commonly available template grid used to guide placement of the needles is a relatively thick block (approximately 2 cm in thickness) of plastic or metal with multiple machined parallel holes arranged in a matrix and spaced at 5 mm intervals. An example of such a template grid is the needle guidance template used with the ULTRA-STEP™ stepping device available from Civco Medical Instruments of Kalona, Iowa. The template grid needs to be thick to have accurate needle placement by ensuring the needle is inserted perpendicular to the face of the template grid. As these block template grids are reused on different patients, one area of potential risk is microbial cross-contamination. Although the template grids are chemically and physically washed and then sterilized between uses, the geometry and small size of the needle holes in the matrix makes reliable sterilization extremely difficult. As the cleaning and sterilization procedures can be quite time consuming, a reusable template grid has a significant amount of "down time" during which it cannot be used.

A disposable template grid would essentially eliminate the possibility of cross-contamination and the other problems associated with reusable grids. The expense of drilling multiple small diameter parallel holes through a thick and hard material makes production of a disposable template grid commercially unfeasible.

As one of the major barriers to eliminating contamination in a reusable template grid is the thickness of the grid and the small diameter of the holes, some manufacturers have tried to circumvent this problem by using a series of thin plates held in parallel and aligned by welded or machined brackets. One example of such a design is the template available with the brachytherapy ultrasound system sold by Carolina Medical Inc. of King, N.C. Spacing the plates apart from each other ensures that the needles are inserted perpendicular to the face of the template grid.

The multi-plate design does make cleaning and sterilization less problematic and also eliminates some of the manufacturing difficulties of the thick block design. The down time due to cleaning and sterilization, however, remains essentially unaffected. Furthermore, the manufacturing costs involved in accurately and securely aligning, spacing, and joining the plates make producing a disposable multi-plate template grid unrealistic.

As the previous discussion illustrates, there exists a need for a sterile disposable template grid system, which need is satisfied by this invention.

SUMMARY OF THE INVENTION

In a first embodiment, the disposable template grid according to the present invention includes a front portion having a plurality of front channels, a rear portion having a plurality of rear channels, and an attachment element for joining the front and rear portions together. Each of the front and rear channels is configured and dimensioned to receive a medical implant so that when the front and rear portions are joined, the front channels align with the rear channels to form a plurality of passages therebetween to allow the medical implant to pass from and through the front portion to and through the rear portion.

Preferably, each front channel has a first opening on a first surface of the front portion connected by a front tubular member to a second opening on a second surface of the front portion and each rear channel has a first opening on a first surface of the rear portion connected by a rear tubular member to a second opening on a second surface of the rear portion. In a preferred embodiment, the attachment element comprises a shoulder extending along an edge on the second surface of the front portion and a groove extending along an edge on the second surface of the rear portion so that the shoulder engaging the groove to join the front and rear portions. In another preferred embodiment, a portion of either the front or rear tubular member has an enlarged diameter configured and dimensioned to receive a portion of the other tubular member to ensure proper alignment of the front and rear channels when the front and rear portions are joined.

The front and rear portions of the disposable template grid are each preferably made of plastic. The attachment element comprises a protuberance located on one of the front and rear portions, and a recess located on the other of the front and rear portions, with the protuberance and recess being positioned, configured and dimensioned for mating engagement to align and releasably join the front and rear portions together. The front portion and/or the rear portion can include a plurality of markers to identify each of the plurality of passages. Preferably, at least one end of each of the passages is chamfered to guide the medical implants from the front portion to the rear portion.

In another embodiment, the disposable template grid according to the present invention comprises an insert having a plurality of channels, a bracket configured and dimensioned for removably receiving and supporting the insert and having a front surface with a plurality of apertures and an alignment element for aligning the plurality of apertures with the plurality of channels to allow a medical implant to pass from one of the plurality of apertures through one of the plurality of channels.

In a preferred embodiment, the insert further comprises a front section having a plurality of front tubes connected to a rear section having a plurality of rear tubes, the front tubes aligning with the rear tubes to form the plurality of channels.

Preferably, the alignment element comprises a groove on a side of the insert and a fastener on a side of the bracket so that the fastener engages the groove to align and releasably secure the insert in the bracket. The alignment element can also comprise at least one slot on a side of the insert which engages at least one pin on a side of the bracket to align and secure the insert in the bracket.

Preferably, the front surface of the bracket has a plurality of markers to identify each of the plurality of apertures and at least one end of each of the channels is chamfered.

The disposable template grid can include at least one mating element for connection to a grid supporting member. The mating element preferably comprises at least one prong.

BRIEF DESCRIPTION OF THE DRAWINGS

The present invention is described in detail below with reference to the drawings in which.

DETAILED DESCRIPTION OF THE PREFERRED EMBODIMENTS

Figure 1:
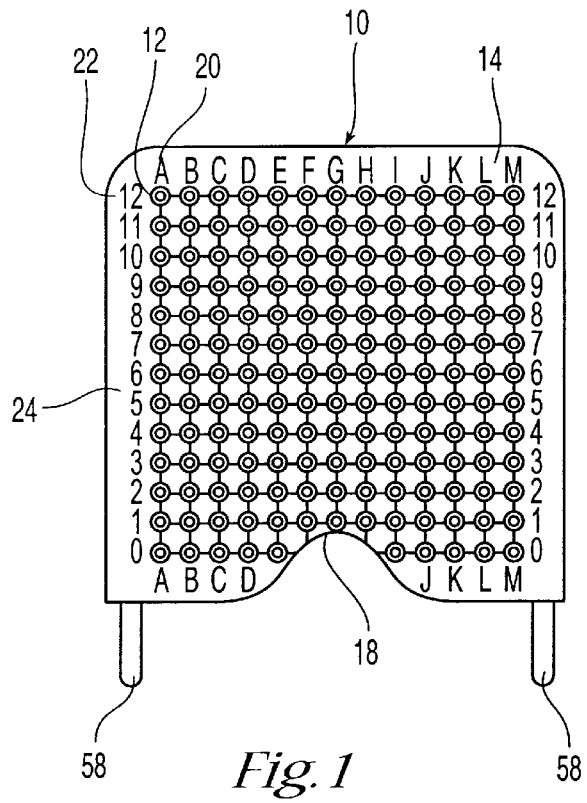
FIG. 1 is a front view of one embodiment of the disposable template grid system according to the present invention.
Figure 2:
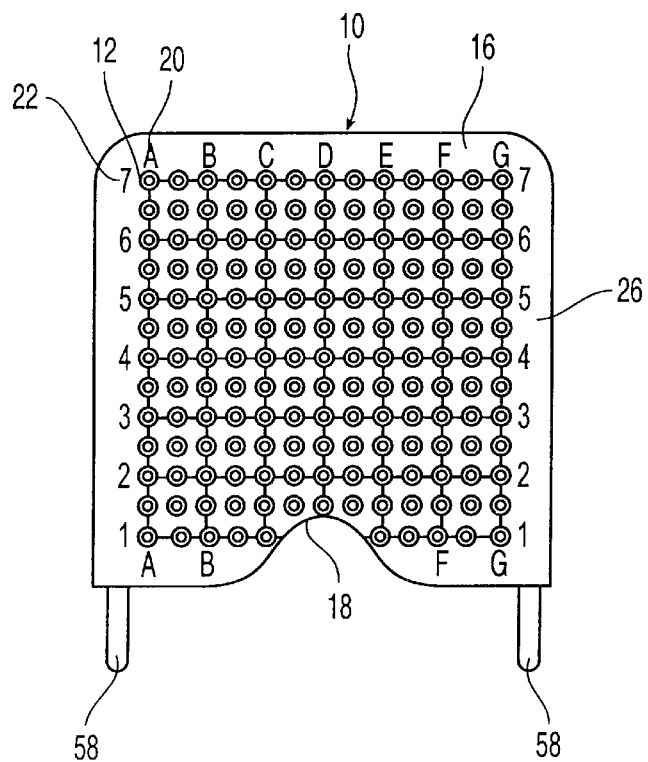
FIG. 2 is a back view of the disposable template grid system of FIG. 1.
Figure 3:
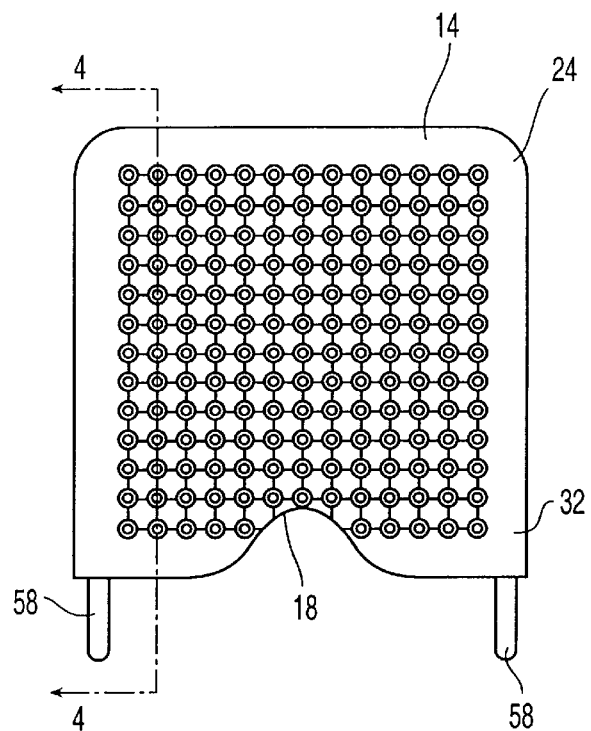
FIG. 3 is a front view of the front portion of the disposable template grid system of FIG. 1.
Figure 4:
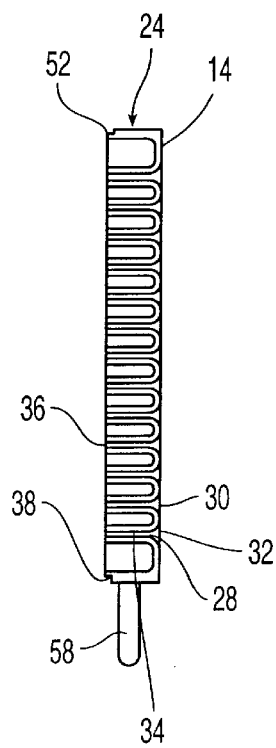
FIG. 4 is a cross-sectional view taken along line A—A of FIG. 3.

FIGS. 1 and 2 show generally a first embodiment of a disposable template grid 10 according to the present invention. Template grid 10 has a series of passages 12 extending from a front 14 through a back 16. Passages 12 are sized to accommodate a medical implant such as seed-containing needles and can be chamfered at front 14 and/or back 16 to facilitate insertion of the implant. Passages 12 are arranged in a pattern corresponding to a software-generated pattern superimposed on images from an imaging probe. A recess 18 for providing clearance for a portion of the probe interrupts the matrix in which passages 12 are arranged.

In order to help the user distinguish the passages 12 from each other, front 14 and back 16 have letters 22 identifying the various columns of passages 12 and numbers 24 identifying the various rows of passages 12. As users have different preferences for the manner in which passages 12 are identified, the configuration of the letters 20 and numbers 22 on front 14 need not be identical to the configuration on back 16. Letters 20 and numbers 22 can be made on front 14 and back 16 by a number of methods including silk screening, molding, engraving, or chemical etching. Any other method which provides a permanent placement of these indicia on the template can be used.

As shown in FIGS. 3–6, front 14 of template grid 10 comprises a front portion 24 and back 16 of template grid 10 comprises a rear portion 26. Front portion 24 includes front channels 28. Each of the front channels 28 has a first opening 30 on a first surface 32 connected by a front tubular member 34 to a second opening 36 on a second surface 38. Similarly, rear portion 26 includes rear channels 40. Each of the rear channels 40 has a first opening 42 on a first surface 44 connected by a rear tubular member 46 to a second opening 48 on a second surface 50.

Figure 5:
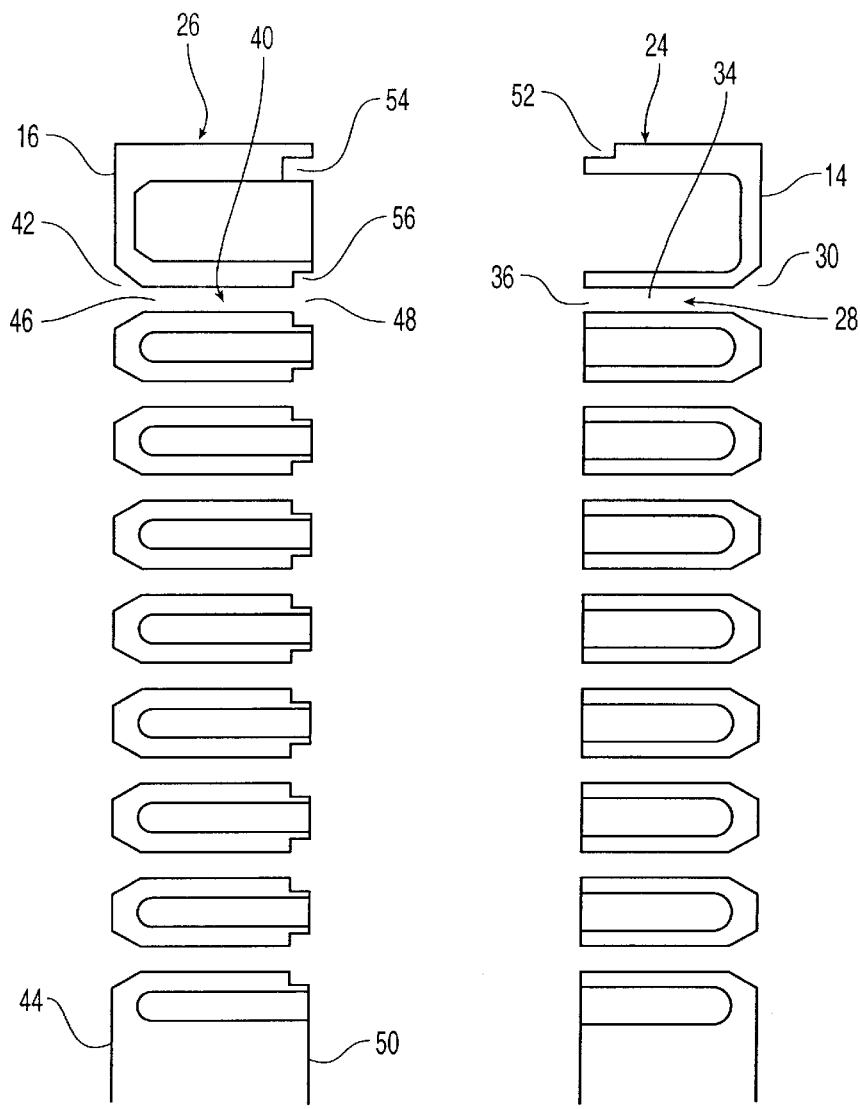
FIG. 5 is an enlarged cross-sectional view of part of the front and rear portions before they are joined.
Figure 6:
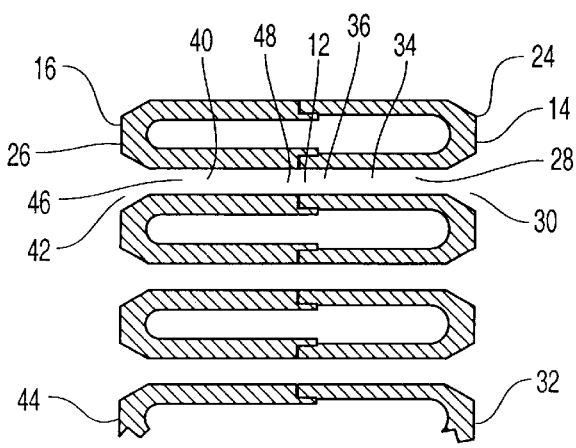
FIG. 6 is a further enlarged cross-sectional view of the front and rear portions after they are joined.
Figure 7:
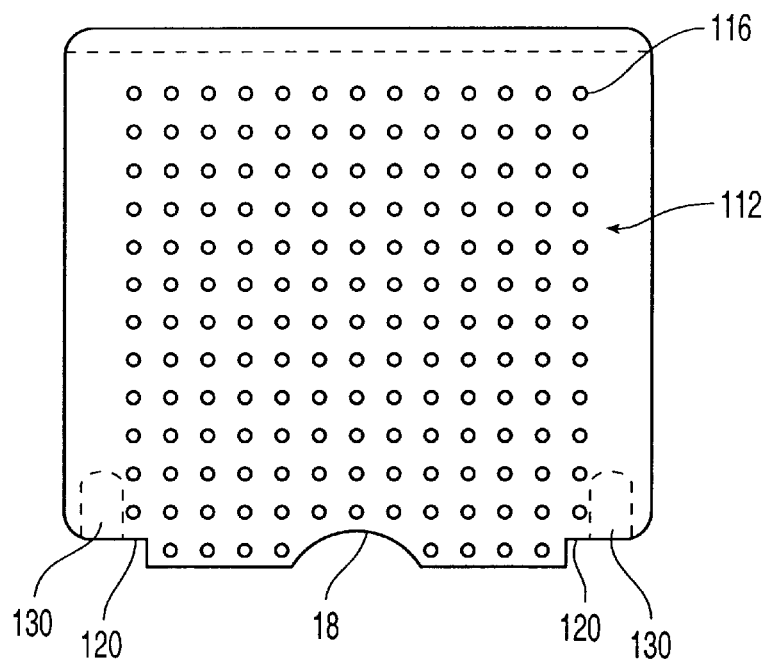
FIG. 7 is a front view of an insert of another embodiment of the device of the present invention.
Figure 8:
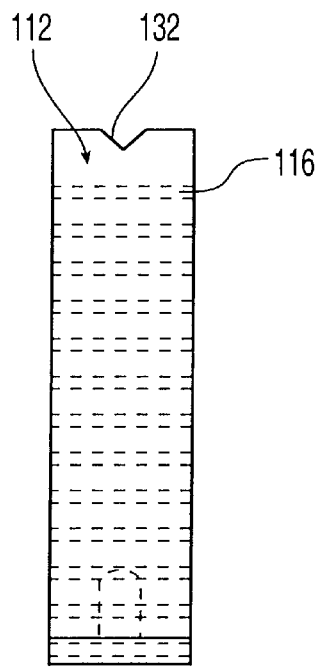
FIG. 8 is a side view of the insert shown in FIG. 7.
Figure 9:
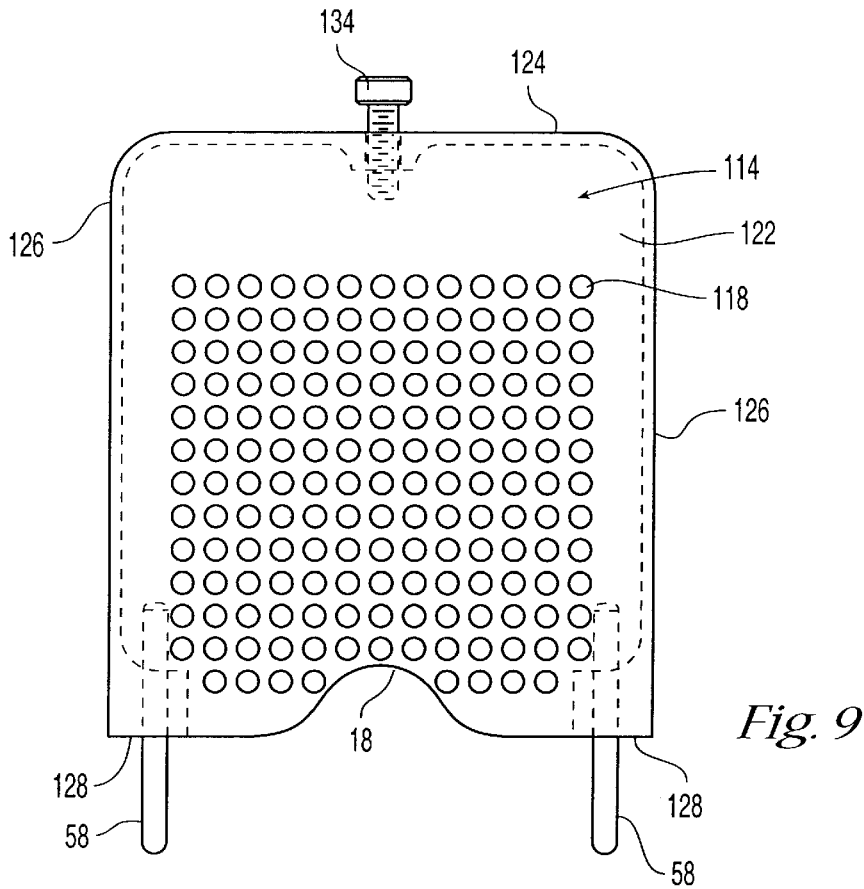
FIG. 9 is a front view of a bracket for use with the insert shown in FIG. 7 and FIG. 8.
Figure 10:
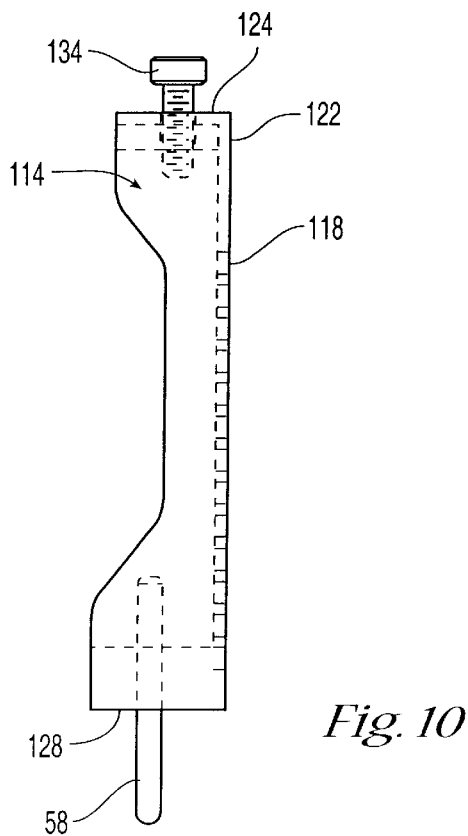
FIG. 10 is a side view of the bracket.

As best seen in FIG. 6, when front 24 and rear 26 portions are joined together, the front channels 28 align with the rear channels 40 to form passages 12. There are a number of different ways in which front portion 24 can be attached to rear portion 26 so that front 28 and rear 40 channels proper align. For example, a shoulder 52 on second surface 38 of front portion 24 engages a groove 54 on second surface 50 of rear portion 26 to connect front 24 and rear 26 portions. Alternatively, shoulder 52 can be on rear portion 26 while groove 54 is on front portion 24. In the embodiment of FIGS. 5 and 6, a portion of rear tubular member 46 has an enlarged diameter 56 for receiving a portion of front tubular member 34. An adhesive can be used to secure front 24 and rear 26 portions.

As previously discussed, the effectiveness of the brachytherapy is highly dependent upon accurate placement of the needles. As a result, the diameter of passages 12 and the spacings between the passages 12 have to be carefully controlled. By making template grid 10 in two halves (i.e., a front portion 24 and a rear portion 26) and then mating second surface 38 with second surface 50, the diameter and spacing of passages 12 need only be precisely controlled for a very small distance, i.e., near first surface 32 of front portion 24 and near first surface 44 of rear portion 26. As this allows most of front tubular member 34 and rear tubular member 46 to be made with much larger tolerances without adversely affecting the accuracy in placement and size of passages 12, template grid 10 can be manufactured at a cost and effort that makes disposability commercially practical.

Although there are a number of different materials suitable for front 24 and rear 26 portions, front 24 and rear 26 portions are preferably made of a plastic using an injection molding process. After fabrication, the disposable template grid 10 can be sterilized by steam sterilization, gas sterilization, or irradiation. Presently, gamma-irradiation is the preferred method of sterilization.

Template grid has at least one mating element for connection to a grid supporting member. Generally, at least two mating elements are used. Preferably, a pair of prongs 58 operatively associated with a pair of grooves on the grid supporting member, are used for this connection. A preferred arrangement is shown, but the number and location of prongs 58 can be varied as desired to suit the configuration of the grid supporting member.

FIGS. 7–10 show a second embodiment of a disposable template grid according to the present invention. In general, this embodiment of the disposable template grid has like or comparable structure to disposable template grid 10. Accordingly, like components are given identical references numerals and discussion of these like components is not believed necessary.

The disposable template grid comprises an insert 112 and bracket 114. Insert 112 has a plurality of channels 116 arranged in a matrix and bracket 114 has similarly arranged apertures 118. When insert 112 is installed in bracket 114 as discussed in more detail below, channels 116 and apertures 118 align. As channels 116 and apertures 118 are sized to accommodate a medical implant such as seed-containing needles, the implant can pass through bracket 114 and insert 112. Preferably, the ends of these channels can be chamfered to assist in guiding the medical implant into the channels and facilitate implant insertion. Channels 116 and apertures 118 can both be chamfered, if desired, for this purpose. The conical shape of the chamfer enables the implant to be easily inserted into the channels.

Insert 112 is a substantially rectangular block of material that is sized to fit in bracket 114. The rectangular structure of insert 112 is interrupted by recess 18 and cut-outs 120. Bracket 114 has a front face 122, top 124, and side surfaces 126. The bottom of bracket 114 comprises two ledges 128 which extend only partially toward recess 18 and support cut-outs 120 when insert 112 is installed in bracket 114. Bracket 114 has an open back allowing insert 112 to be installed by sliding insert 112 at an angle until cut-outs 120 rest on ledges 128. In order to further assist installation, sides 126 have an open center section so that insert 112 can be grabbed until it is correctly introduced in bracket 114.

Prongs 58 extend through the top and bottom of ledges 128 of bracket 114. As previously discussed, one end of prongs 58 engages a grid supporting member. Cut-outs 120 of insert 112 each have a slot 130 for receiving the top end of prongs 58. The engagement of slots 130 with prongs 58 ensures proper alignment of channels 116 and apertures 118. A set screw 134 on top 124 of bracket 114 is tightened into a groove 132 on insert 112 in order to secure insert 112 to bracket 114.

Although both insert 112 and bracket 114 can be made to be disposable, it is currently preferred that bracket 114 be reusable. As front face 122 is relatively thin, apertures 118 (and the rest of bracket 114) can be cleaned and properly sterilized. Insert 112 is preferable made of a medical grade plastic which can be machined and sterilized such as acetal or polycarbonate. Insert 112 is discarded after a single use.

Figure 11:
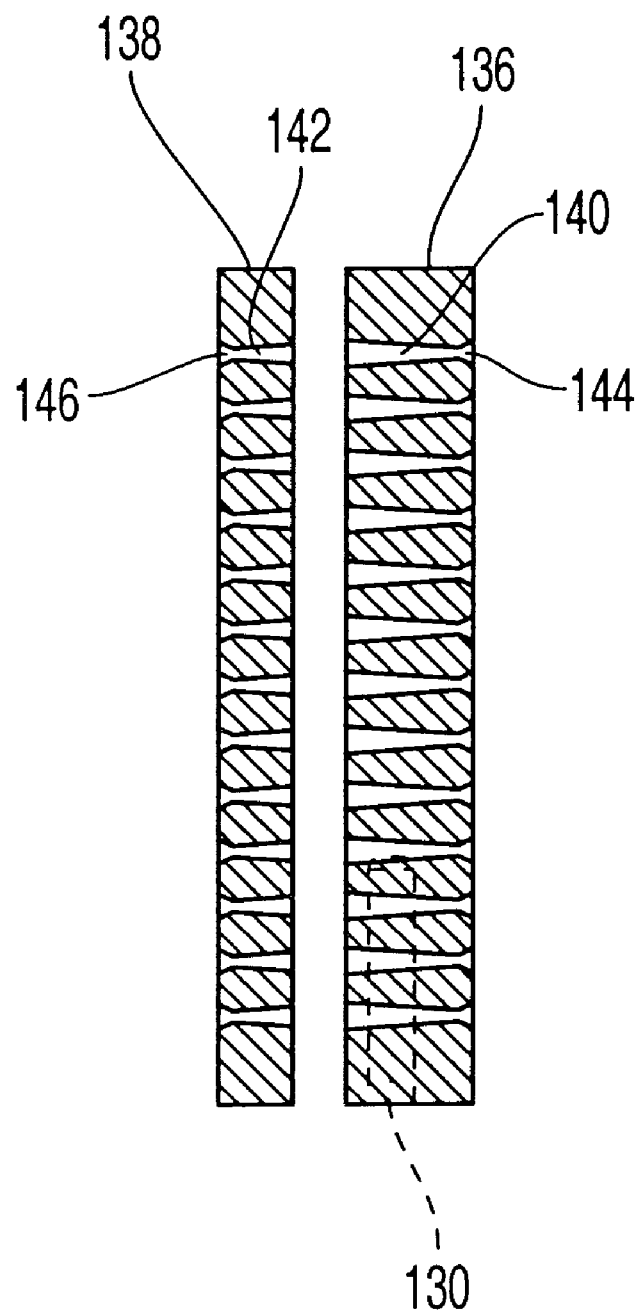
FIG. 11 is a cross-sectional view of another embodiment of the insert.

As shown in FIG. 11, insert 112 can be made in two sections: a front section 136 and a rear section 138. When front 136 and rear 138 sections are joined, front tubes 140 align with rear tubes 142 to form channels 116. As was the case with front 24 and rear 26 portions of disposable template grid 10, there are a number of different ways to join front 136 and rear 138 sections. For example, a shoulder on an outer edge of either front 136 or rear 138 section can engage a groove on the other section. Alternatively, a pin (or pins) on either front 136 or rear 138 section can engage a slot (or slots) on the other section. By making insert 112 in two halves (i.e., front section 136 and rear section 138) and then mating the two halves together, the diameter and spacing of channels 116 need only be precisely controlled for a very small distance, i.e., near an outer surface 144 of front section 136 and near an outer surface 146 of rear section 138. As this allows most of front tubes 140 and rear tubes 142 to be made with much larger tolerances without adversely affecting the accuracy in placement and size of channels 116, insert 112 can be manufactured at a cost and effort that makes disposability commercially practical. Furthermore, if insert 112 is machined, the problems associated with precisely machining small diameter holes on a thick block are avoided.

While the instant invention has been shown and described herein in what are conceived to be the most practical and preferred embodiments, it is recognized that departures, modifications, adaptations and variations may be made therefrom within and without departing from the scope of the invention, which is therefore not to be limited to the details disclosed herein, but is to be afforded the full scope of the claims so as to embrace any and all equivalent apparatus and articles.

What is claimed is:

1. A disposable template grid comprising:

a front portion having a plurality of front channels, each of which is adapted to receive a medical implant;

a rear portion having a plurality of rear channels, each of which is adapted to receive the medical implant; and an attachment element for joining the front and rear portions together, wherein the front channels align with the rear channels to form a plurality of passages therebetween adapted to allow the medical implant to pass from and through the front portion to and through the rear portion when the front and rear portions are joined with at least part of the front portion in contact with at least part of the rear portion.

2. A disposable template grid comprising:

a front portion having a plurality of front channels, each of which is adapted to receive a medical implant;

a rear portion having a plurality of rear channels, each of which is adapted to receive the medical implant; and an attachment element for joining the front and rear portions together, wherein the front channels align with the rear channels to form a plurality of passages therebetween adapted to allow the medical implant to pass from and through the front portion to and through the rear portion when the front and rear portions are joined and wherein the front and rear portions are each made of plastic, and the attachment element comprises a protuberance located on one of the front and rear portions, and a recess located on the other of the front and rear portions, with the protuberance and recess being positioned, configured and dimensioned for mating engagement to align and releasably join the front and rear portions together.

3. A disposable template grid comprising:

a front portion having a plurality of front channels, each of which is adapted to receive a medical implant;

a rear portion having a plurality of rear channels, each of which is adapted to receive the medical implant; and an attachment element for joining the front and rear portions together, wherein the front channels align with the rear channels to form a plurality of passages therebetween adapted to allow the medical implant to pass from and through the front portion to and through the rear portion when the front and rear portions are joined and wherein each front channel has a first opening on a first surface of the front portion connected by a front tubular member to a second opening on a second surface of the front portion; and each rear channel has a first opening on a first surface of the rear portion connected by a rear tubular member to a second opening on a second surface of the rear portion.

4. The disposable template grid of claim 3 wherein the attachment element comprises a shoulder extending along an edge on the second surface of the front portion and a groove extending along an edge on the second surface of the rear portion, said shoulder engaging the groove to join the front and rear portions.

5. The disposable template grid of claim 3 wherein a portion of the front tubular member has an enlarged diameter configured and dimensioned to receive a portion of the rear tubular member to ensure proper alignment of the front and rear channels when the front and rear portions are joined.

6. The disposable template grid of claim 1 wherein the front portion includes a plurality of markers to identify each of the plurality of passages.

7. The disposable template grid of claim 1 wherein the rear portion includes a plurality of markers to identify each of the plurality of passages.

8. A disposable template grid comprising:
a front portion having a plurality of front channels, each of which is adapted to receive a medical implant;
a rear portion having a plurality of rear channels, each of which is adapted to receive the medical implant; and
an attachment element for joining the front and rear portions together, wherein
the front channels align with the rear channels to form a plurality of passages therebetween adapted to allow the medical implant to pass from and through the front portion to and through the rear portion when the front and rear portions are joined and wherein
each passage is adapted to guide the medical implants from the front portion to the rear portion, and the attachment element is an adhesive.

9. The disposable template grid of claim 8 wherein at least one end of each of the plurality of passages is chamfered and adapted to guide the medical implants from the front portion to the rear portion.

10. The disposable template grid of claim 1 further comprising at least one mating element for connection to a grid supporting member.

11. The disposable template grid of claim 10 wherein the mating element comprises at least one prong.

12. The disposable template grid of claim 1 wherein the front and rear portions are made using an injection molding process.

13. A disposable template grid comprising:
an insert having a plurality of channels;
a bracket configured and dimensioned for removably receiving and supporting the insert and having a front surface with a plurality of apertures; and
an alignment element for aligning the plurality of apertures with the plurality of channels adapted to allow a medical implant to pass from one of the plurality of apertures through one of the plurality of channels.

14. The disposable template grid of claim 13, wherein the alignment element comprises a groove on a side of the insert and a fastener on a side of the bracket, the fastener engaging the groove to align and releasably secure the insert in the bracket.

15. The disposable template grid of claim 13, wherein the alignment element comprises at least one slot on a side of the insert and at least one pin on a side of the bracket, the at least one pin engaging the at least one slot to align and secure the insert in the bracket.

16. The disposable template grid of claim 13, wherein the front surface of the bracket has a plurality of markers to identify each of the plurality of apertures.

17. The disposable template grid of claim 13, wherein at least one end of each of the plurality of channels is chamfered.

18. The disposable template grid of claim 13, further comprising at least one mating element for connection to a grid supporting member.

19. The disposable template grid of claim 18, wherein the mating element comprises at least one prong.

20. The disposable template grid of claim 13, wherein the insert further comprises a front section having a plurality of front tubes connected to a rear section having a plurality of rear tubes, the front tubes aligning with the rear tubes to form the plurality of channels.

21. The disposable template grid of claim 20, wherein the front and rear sections are each made of plastic, and further comprising an element for releasably attaching the sections together, the attachment element comprising a protuberance located on one of the front and rear sections and a recess located on the other of the front and rear sections, with the protuberance and recess being positioned, configured and dimensioned for mating engagement to align and join the front and rear sections together.

* * * * *